(12) United States Patent
Baeumer

(10) Patent No.: US 12,363,273 B2
(45) Date of Patent: Jul. 15, 2025

(54) METHOD FOR CREATING A CAMERA MODEL FOR A CAMERA OF A SURGICAL MICROSCOPE, AND ARRANGEMENT HAVING A SURGICAL MICROSCOPE

(71) Applicant: Carl Zeiss Meditec AG, Jena (DE)

(72) Inventor: Richard Baeumer, Schorndorf (DE)

(73) Assignee: Carl Zeiss Meditec AG, Jena (DE)

( * ) Notice: Subject to any disclaimer, the term of this patent is extended or adjusted under 35 U.S.C. 154(b) by 455 days.

(21) Appl. No.: 17/745,519

(22) Filed: May 16, 2022

(65) Prior Publication Data

US 2022/0368884 A1 Nov. 17, 2022

(30) Foreign Application Priority Data

May 17, 2021 (DE) ...................... 10 2021 112 737.8

(51) Int. Cl.
*H04N 17/00* (2006.01)
*A61B 90/20* (2016.01)
(Continued)

(52) U.S. Cl.
CPC .......... *H04N 17/002* (2013.01); *A61B 90/20* (2016.02); *G06T 7/70* (2017.01); *G06T 7/80* (2017.01);
(Continued)

(58) Field of Classification Search
CPC ...... H04N 17/002; A61B 90/20; A61B 90/25; A61B 2017/00725; A61B 2034/2055;
(Continued)

(56) References Cited

U.S. PATENT DOCUMENTS 10,369,698 B1 * 8/2019 Islam .................. G06T 7/50
10,399,227 B1 * 9/2019 Islam .................. B25J 9/1692
(Continued)

FOREIGN PATENT DOCUMENTS

DE 102018115824 A1 1/2020
DE 102020106973 A1 10/2020
(Continued)

OTHER PUBLICATIONS

ISO, "DIN EN ISO 8373, Robotics—Vocabulary", International Standard, (2021), pp. 1-30, Third Edition, ISO 8373:2021 (E), Switzerland.
(Continued)

*Primary Examiner* — Juan A Torres
(74) *Attorney, Agent, or Firm* — Ewers IP Law PLLC; Falk Ewers

(57) ABSTRACT

A method for creating a camera model for a camera of a surgical microscope includes positioning a calibration object in an initial pose in an observation region of the camera, determining a pose delta for reaching a first pose for the calibration object in a measurement space of the camera starting from the initial pose, positioning the calibration object in the first pose in accordance with the determined pose delta, making a recording of the calibration object in the first pose with the camera, positioning the calibration object in at least one further pose, making a recording of the calibration object in the at least one further pose, and creating a camera model based on the recordings made, the first pose and the at least one further pose being chosen with a distribution in the measurement space such that a camera model is obtained which represents the entire measurement space.

14 Claims, 12 Drawing Sheets

(51) Int. Cl.
*G06T 7/70* (2017.01)
*G06T 7/80* (2017.01)

(52) U.S. Cl.
CPC ............ *G06T 2207/10016* (2013.01); *G06T 2207/10056* (2013.01); *G06T 2207/30204* (2013.01); *G06T 2207/30244* (2013.01)

(58) Field of Classification Search
CPC ..... A61B 2090/3937; G06T 7/70; G06T 7/80; G06T 2207/10016; G06T 2207/10056; G06T 2207/30204; G06T 2207/30244; G06T 2207/30004; G06T 2207/30208; G02B 21/0012
USPC ........................................................ 382/128
See application file for complete search history.

(56) References Cited

U.S. PATENT DOCUMENTS

| | | | |
|---|---|---|---|
| 11,014,241 B2 | 5/2021 | Islam et al. | |
| 11,554,494 B2* | 1/2023 | Goller | B25J 9/1653 |
| 11,590,656 B2* | 2/2023 | Islam | G06T 7/80 |
| 2005/0215879 A1* | 9/2005 | Chuanggui | G06T 17/00 |
| | | | 600/407 |
| 2017/0258529 A1* | 9/2017 | Winne | A61B 17/00234 |
| 2020/0004003 A1 | 1/2020 | Omlor et al. | |
| 2020/0282575 A1* | 9/2020 | Haeusler | B25J 9/1612 |
| 2021/0122050 A1 | 4/2021 | Islam et al. | |
| 2021/0157112 A1 | 5/2021 | Raab et al. | |
| 2023/0260158 A1* | 8/2023 | Stopp | A61B 34/20 |
| | | | 382/128 |
| 2023/0390021 A1* | 12/2023 | Polchin | A61B 90/94 |

FOREIGN PATENT DOCUMENTS

| | | |
|---|---|---|
| DE | 102020106968 A1 | 4/2021 |
| DE | 102019131646 A1 | 5/2021 |
| EP | 3706080 A1 | 9/2020 |
| WO | 2022033656 A1 | 2/2022 |
| WO | 2022043896 A2 | 3/2022 |

OTHER PUBLICATIONS

Office Action issued in German Patent Application No. DE 10 2021 112 737.8, dated Feb. 8, 2022 (from which this application claims priority) and English language translation thereof.

* cited by examiner

METHOD FOR CREATING A CAMERA MODEL FOR A CAMERA OF A SURGICAL MICROSCOPE, AND ARRANGEMENT HAVING A SURGICAL MICROSCOPE

CROSS REFERENCE TO RELATED APPLICATIONS

This application claims priority to German patent application DE 10 2021 112 737.8, filed May 17, 2021, the entire content of which is incorporated herein by reference.

TECHNICAL FIELD

The disclosure relates to a method for creating a camera model for a camera of a surgical microscope, to a method for estimating a pose of an object in a measurement space of a camera of a surgical microscope, to a method for verifying a camera model, to an arrangement having a surgical microscope, to a computer program and to a computer-readable medium.

BACKGROUND

Surgical microscopes are used in various medical disciplines, such as ophthalmic surgery, dental surgery or neurosurgery. On account of the increasing complexity of surgical microscopes, there is an increased need for testing, adjustment and calibration methods to test the functionality and to be able to undertake changes or apply specific settings where necessary. These methods, which are subsumed by the term calibration method below, can be carried out during the intended use of the surgical microscope, or else within the scope of manufacture, and servicing and upkeep.

Calibration methods within the aforementioned meaning may include, inter alia: diopter settings on the eyepiece, verifying and setting the X, Y, Z-position of cameras and other optical components, verifying and setting intrinsic camera parameters, temporal calibration of cameras, verifying and setting zoom and autofocus, establishing the absolute fluorescence intensity, verifying and setting the kinematics of the stand for improving the absolute positioning accuracy.

By way of example, the accuracy of pose estimates is decisively influenced by the intrinsic calibration of the camera. Important parameters, for example the position of the camera chip relative to the optical axis of the camera system and distortion coefficients, are determined within the scope of the intrinsic calibration on the basis of recordings of a calibration object, which is also referred to as calibration standard, calibration target or marker. The quality of the parameter determination, i.e., the measure for the deviation between the determined parameter and the actual parameter, depends, inter alia, on the pose from which the recordings are made.

To verify and set the surround camera for tracking instruments, the (hand-held) surgical instrument to be tracked is provided with a two-dimensional (2D) calibration object. The calibration object is filmed by a camera attached to the microscope and its relative position in the operating field is calculated. With appropriate driving of the motor-driven stand of the microscope, it is possible for the optical axis of the microscope to track the tip of the surgical instrument.

The intrinsic calibration of the surround camera is required to facilitate this. The intrinsic parameters serve to re-establish the relationship between the camera coordinate system and image coordinate system. Moreover, the distortion coefficients of the optical unit can be determined.

A further precondition for tracking instruments is the calibration between the coordinate origin of the surround camera and a physical point on the microscope since the movement of the instrument, as recognized by the surround camera, must be implemented in the coordinate system of the microscope. On account of the coordinate origin of the surround camera corresponding to no physical point on the surround camera, this cannot be measured geometrically. Therefore, methods such as the hand/eye calibration are required to carry out this calibration.

To check and set internal cameras, for example for the topographic reconstruction of the surface of the site with at least two cameras of a stereoscopic microscope or for expanded representations (augmentation), an intrinsic calibration (see the explanation above) and an extrinsic calibration are required. In the case of the extrinsic calibration, the spatial arrangement of the cameras, i.e., the rotation and translation thereof, with respect to one another is determined. Since the cameras in a surgical microscope are arranged in the optical path downstream of a movable lens system for zoom and focus, there is a particular challenge in carrying out the calibration for arbitrary zoom and focus values, and in compensating tolerances in the motors which move the lenses for zoom and focus. An accurate calibration is also required if image data of a camera should be superposed on image data of another camera or be used for augmentation purposes thereon.

The quality of the results of some applications depends on the absolute positioning accuracy of the stand of the microscope. Examples of this include the pivoting of the microscope about the focal point or the off-line positioning in relation to certain poses in space, e.g., within the scope of tool tracking. The absolute positioning accuracy of the stand depends, in turn, on the exact knowledge of the kinematic parameters of the stand, which may deviate from the nominal values on account of usual assembly and manufacturing tolerances.

By way of example, the stand kinematics can be calibrated by virtue of one or more defined points in space being approached in different orientations of the stand. In the specific example of a surgical microscope, this can be realized by virtue of the optical unit of the surgical microscope being aligned on a calibration object. Together with the camera calibration, it is then possible to determine the actual pose and orientation of the surgical microscope relative to the calibration object. In knowledge of the fact that the calibration object is arranged at the same locations in all poses, the deviation of the actual pose from the nominal pose of the surgical microscope represents the variable of the calibration algorithm to be minimized. To be able to calibrate a larger working region, it is also possible to use a plurality of calibration objects with the fixed and known pose in relation to one another.

The calibration methods known from the prior art are based on random recordings of the calibration object, using which more or less successful attempts are made to map the measurement space of the camera. To this end, a calibration object is arranged in the volume observable by the camera, independently of the size and position of the measurement space. This leads to a camera model based on such recordings not reproducibly mapping the entire measurement space. Inaccuracies arise in the underrepresented regions of the measurement space. Moreover, currently available methods do not allow an automated calibration of a surgical microscope in the region of use.

Making recordings from different observation angles and/or different distances for calibration purposes has only been disclosed in the subsequently published German patent application with the file reference 10 2019 131 646.4, filing date: 22 Nov. 2019, by the applicant of the present application. This procedure can be implemented automatically, for example by virtue of a robotic stand being used to align the optical observation unit.

SUMMARY

Against this background, it is an object of the present disclosure to provide a method that can be used to create a camera model for a camera of a surgical microscope, the model having a high accuracy over the entire measurement space. Further objects of the present disclosure are providing a method for estimating a pose of an object in a measurement space of a camera of a surgical microscope, providing a method for verifying a camera model, an arrangement, and providing a computer program.

The objects are achieved by a method for creating a camera model for a camera of a surgical microscope, a method for estimating a pose of an object, a method for verifying a camera model, an augmentation, an arrangement, and a non-transitory computer-readable storage medium as described herein.

A first aspect of the disclosure relates to a method for creating a camera model for a camera of a surgical microscope. The method includes the following method steps: positioning a calibration object in an initial pose in an observation region of a camera of the surgical microscope, determining a pose delta for reaching a first pose for the calibration object in a measurement space of the camera starting from the initial pose, positioning the calibration object in the first pose in accordance with the determined pose delta, making a recording of the calibration object in the first pose with the camera, positioning the calibration object in at least one further pose in the measurement space of the camera, making a recording of the calibration object in the at least one further pose with the camera, and creating a camera model on the basis of the recordings made. In this case, the first pose and the at least one further pose are chosen with such a distribution in the measurement space that a camera model is obtained which is representative in relation to the entire measurement space.

The method can be carried out in computer-implemented fashion, that is to say at least one method step can be carried out by a computer program.

A camera model is representative in relation to the entire measurement space if the pose of an object whose geometry and actual pose are known can be estimated in such a way with the aid of this model that the error in the pose estimate, that is to say the deviation between the estimated pose and the actual pose, is below a target limit in the demanded measurement space, that is to say a specifiable quality of the camera model is achieved. Should the pose estimate have an error, the latter is typically of the same magnitude in the entire measurement space.

In an exemplary embodiment, the surgical microscope includes one or more cameras with associated stands. The cameras can be used to generate photographs or films of an observation object or observation region, for example the site. To this end, the camera includes an image sensor or image chip and a lens. The camera can be a surround camera, for example a surround camera with a fixed focal length and without a zoom system, or a microscope camera.

A surround camera can be understood to mean a camera whose measurement space images the surround of the operating site, and which can be used for tool tracking, for example. A microscope camera can be understood to mean a camera which images the immediate operating site, in particular imaging the latter in a magnified fashion. The microscope camera may also be referred to as principal observer. The measurement space of the microscope camera usually has a smaller volume than the measurement space of the surround camera. By way of example, the diameter of the cylindrical measurement space of the microscope camera may be smaller than the diameter of the cylindrical measurement space of the surround camera.

Consequently, the method can be used to create a camera model of a surround camera or a microscope camera. Optionally, the method can be used to create a camera model both for the surround camera and for the microscope camera. For the latter variant, a camera model for the surround camera can initially be created in accordance with the method and a camera model for the microscope camera can subsequently be created in accordance with the method, the sequence also being able to be chosen in reverse. Moreover, there is the option of initially creating a camera model according to the method for one of the two cameras, that is to say the surround camera or the microscope camera, and of creating a camera model for the respective other camera of the two cameras on the basis of this camera model created first, by virtue of implementing geometric transformation of the coordinate system of the one camera into the coordinate system of the other camera.

A stand serves to position, align and hold a camera. To this end, the camera can be connected to the stand with a mount. To fulfil this task, the camera held by the stand should firstly be able to be positioned with as little resistance as possible. Secondly, the camera, once positioned, should be able to be held securely in its position. Additionally, the stand can fulfil other tasks, for example of facilitating a tracking of instruments by virtue of the camera being moved in a targeted fashion with the stand.

In order to be able to fulfil these tasks, the stand includes a plurality of stand links, interconnected in secured or articulated fashion, for example a height-adjustable stand column, a support arm, a spring arm, and a mount for the optical observation unit. Moreover, provision can be made of a stand base, on the underside of which devices, e.g., rollers, for displacing the stand may be attached. The specific embodiment of the stand depends, inter alia, on the dimensions of the camera, the desired application, e.g., during an operation, and the space available at the setup location.

The stand can have a motor-driven configuration such that positioning and alignment of the camera can be facilitated by an appropriate control of the motors of the stand. For this purpose, the stand can be signal-connected to a control unit.

By moving the stand, it is likewise possible to move the camera, and so different observation positions can be adopted.

Optionally, the surgical microscope may include a control unit that is configured and designed to output control signals to the stand and/or the camera, for example to carry out the method for creating a camera model or the method, described below, for calibrating a surgical microscope.

To this end, there can be a signal-transmitting operative connection between the control unit and motors of the stand and/or adjustment devices of the camera such that it is possible to output control signals which bring about certain positioning of the stand and the camera.

By way of example, the output of the control signals can be implemented as a consequence of an input using an input unit connected to the control unit, for example should a user manually initiate one of the aforementioned methods by way of an appropriate input. Alternatively, the control signals can be output in response to the presence of other triggers, e.g., expiry of a specifiable time interval, expiry of a specifiable use duration of the surgical microscope, a change in the location of the surgical microscope, an excessive deviation of an actual value from a target value, etc.

The control unit facilitates a partly or fully automated implementation of the specified methods, and so the said methods can be carried out with little outlay in terms of time and staff, e.g., even without the presence of the user. Thus, calibration methods can also be carried out outside of the period of use of the surgical microscope, e.g., at night or over the weekend. Moreover, the number of error sources is reduced as a result of the automation, since a user intervention is not required or only required to a small extent. The reliability and reproducibility of the measurement results obtainable by the surgical microscope can be increased as a result.

In conjunction with the present disclosure, a calibration object has at least one characteristic marking, typically a plurality of characteristic markings, for example corners of a chequerboard pattern, the properties of which, e.g., size, distance, and alignment, are known accurately. By way of example, the calibration object can be in the form of a two-dimensional calibration pattern or three-dimensional calibration body.

By way of example, a two-dimensional calibration pattern can be embodied as a chequerboard pattern, a point pattern, a QR code, a logo, or the like. It is easily and cost-effectively possible to produce such a calibration pattern and to arrange the latter optionally also on a stand of the surgical microscope, e.g., with printing, laser engraving or adhesive bonding. Furthermore, there is the option of cost-effectively representing a two-dimensional calibration pattern on a monitor, with this rendering a simple change between different calibration patterns possible. Moreover, already available monitors can be used for the representation.

A three-dimensional calibration body can include a main body that is transparent in the spectral range employed, i.e., for example, in the visible spectral range, and one or more non-transparent calibration marks arranged in the main body. Such a calibration body facilitates a calibration in three dimensions. In respect of further details of possible three-dimensional calibration bodies, reference is made to the German patent application DE 10 2018 115 824 A1, which describes such calibration bodies in detail.

The calibration object can be configured such that the characteristic markings are visible in the visible spectral range, e.g., in a conventional white-light image. In addition or as an alternative to the visible spectral range, the characteristic markings may be visible in a different spectral range, e.g., in the infrared spectral range.

The calibration object can have a passive, i.e., always present, form, e.g., as a printed pattern, or it can have an activatable and deactivatable form. Activatable and deactivatable means that the calibration object or the structures, marks, etc., used for the calibration can be activated or deactivated according to need, e.g., by targeted driving of light-emitting diodes or in the form of a calibration pattern that is dynamically displayed on a monitor.

In conjunction with the present disclosure, the term "pose" is understood to mean the combination of position and orientation of the specified objects or components or reference axes in three-dimensional space (see also DIN EN ISO 8373). The position of a punctiform mass in relation to a Cartesian coordinate system is accordingly defined by the distances in the coordinate directions x, y, z. If a second Cartesian coordinate system is spanned at this point of mass, the orientation of this coordinate plane is defined by the angular offset of the latter's coordinate axes in relation to the corresponding axes of the base coordinate system. Three angles are additionally required, these describing the relative position of the new coordinate system in relation to the base coordinate system.

In the present case, the term "measurement space" is understood to mean the volume to be observed with the camera, that is to say the region in which the processes to be observed take place and for which a calibration must be available, for example in order to be able to uniquely determine distances. The maximum region able to be imaged with the camera may be larger by comparison, that is to say the measurement space is restricted to a part of the volume even observable with the camera. In the present case, the volume observable with the camera is referred to as "observation region".

The measurement space may be defined in the coordinate system of the camera for which a camera model is created in accordance with the proposed method. Alternatively, the measurement space may be defined in the coordinate system of a further camera of the surgical microscope. For the latter alternative, the positioning of this further camera in relation to the camera for which the camera model is created must be known, that is to say the geometric transformation from the coordinate system of the further camera, e.g., the microscope camera, to the coordinate system of the camera for which the camera model is created, e.g., the surround camera, must be known.

By way of example, the measurement space may have a cylindrical form. Depending on the distance from the camera, the measurement space can be subdivided into a near region and a remote region. By way of example, the near region may be localized between 0% and 30% of the longitudinal extent of the measurement space along the optical axis of the camera and the remote region, by contrast, may be localized between 70% and 100%.

In the first method step of the provided method, a calibration object is positioned in an initial pose in the observation space of the camera, that is to say the calibration object positioned in the initial pose may also be located outside of the measurement space for as long as it is detectable by the camera. The initial pose can be chosen as desired within the observation region. The initial pose can be estimated with an initial camera model or a nominal camera model.

In the next step, the pose delta between the initial pose and a first pose is determined, that is to say the pose delta that is required to reach the first pose starting from the initial pose. In this case, the pose delta corresponds to the vector according to which the calibration object needs to be moved in order to convert the initial pose into the first pose. Optionally, a transformation of the coordinate systems to one another needs to be taken into account, depending on the camera coordinate system in which the measurement space is defined. Subsequently, the calibration object is positioned in the first pose in accordance with the determined pose delta. To this end, the pose delta can be controlled with the stand of the surgical microscope, for example, in order to change the camera pose and hence indirectly change the pose of the calibration object. In contrast to the initial pose, the calibration object positioned in the first pose is necessarily at least partially within the measurement space.

In a further step, a recording, for example a photographic or video recording, of the calibration object is made. Optionally, the calibration object can be activated before the recordings are made, for example by virtue of the calibration object being illuminated or a self-luminous calibration object being activated to shine.

Subsequently, these two steps are repeated for at least one further pose. In this case, the overall number of poses depends, inter alia, on the number of characteristic markings on the calibration object (the more markings, the fewer poses are required), the size of the measurement space (the larger the measurement space, the more poses are required) and the required accuracy or quality of the camera model (the higher the accuracy, the more poses are required). By way of example, the overall number of poses can range between 20 and 25.

The recordings made are subsequently evaluated and a camera model is created on the basis of the totality of the recordings made. The camera model describes, inter alia, the properties of the image sensor of the camera and of the camera optics, and the arrangement of image sensor and optics in relation to one another. To this end, the camera model includes values for calibration parameters, that is to say correction factors, with which it is possible to take account of the relationship between a beam in the measurement space of the surgical microscope, more precisely in the measurement space of the camera of the surgical microscope, and a point on the image sensor of the camera. A pinhole camera model may form the basis to this end, that is to say a deviation from a nominal pinhole camera model can be compensated with the calibration parameters obtained in the camera model. Expressed differently, the camera model may include values for calibration parameters, that is to say correction factors, with which it is possible to take account of the relationship between the position of the optical center according to the pinhole camera model and a point on the image sensor of the camera. Moreover, the camera model may include correction factors that can be used to correct distortions, so-called distortion coefficients.

By way of example, the camera model may include values for the following calibration parameters: distance between image sensor of the camera and optical center in the x-direction, y-direction, and z-direction, and distortion coefficients.

Optionally, provision can be made for the value of a quality parameter to be determined for the camera model created from the totality of the recordings made. By way of example, this value of the quality parameter can be used to ensure a certain tracking or data overlay quality. To this end, the established value of the quality parameter can be compared to a specifiable target value or limit value.

To create the camera model, the characteristic markings of the calibration object can be recognized with the aid of suitable algorithms in a recording of the calibration object and can be assigned to one another. Thus, the points in the image of the recording corresponding to the characteristic markings and the geometry of the calibration object are known. The calibration parameters can be determined therefrom with an optimization algorithm, so that the camera model maps the transformation of the calibration object on the image sensor of the camera to the best possible extent. In this case, the optimization algorithm can take account of not only one recording, but of a plurality or all recordings of the calibration object in the various poses.

The made recordings can be evaluated in computer-implemented or software-based fashion, either in the surgical microscope itself or with an external evaluation unit, which is signal-connected to the surgical microscope.

Provision is made for the first pose and the at least one further pose to be chosen with such a distribution in the measurement space, i.e., defined in a targeted manner, that a camera model is obtained which is representative in relation to the entire measurement space.

Expressed differently, it is not only a certain number of poses of the calibration object that are defined, and corresponding recordings are made, but the poses to be adopted are determined in a targeted fashion to the effect of the measurement space being sufficiently accurately represented at all points, i.e., that no region of the measurement space is overweighted or underweighted. Sufficiently accurately means that the accuracy for a pose estimate for which the camera model is used is above a certain limit, i.e., the error of the pose estimate in the required measurement space is below a target limit. Symmetries of the measurement space can be taken into account in the process.

As a result, a camera model with a high accuracy or calibration quality is advantageously created since the values for the calibration parameters can be estimated better, i.e., more accurately, and with a greater reproducibility for the entire measurement space. This directly has an effect on the quality of the pose estimates and measurements carried out using such a camera model, said pose estimates and measurements likewise being more accurate and having a greater reproducibility accordingly.

The targeted definition of the poses moreover facilitates an automation of the method since there is no need for a manual movement of the calibration object and/or of the surgical microscope. This may also contribute to an increase in the reproducibility over random recordings. Moreover, the method can even be started by non-specialist staff, for example a theatre nurse, e.g., by operating a simple start button. The method can likewise be carried out within the scope of remote maintenance.

Typically, the camera model can be created with a single calibration object as the latter is usable multiple times in various poses.

Moreover, the calibration object may have a transportable design, that is to say it is not connected to the surgical microscope, e.g., the stand thereof. Connectability of the calibration object to the surgical microscope or a body arranged in stationary fashion in relation to the surgical microscope, for example a wall, etc., for the purposes of facilitating a certain pose in relation to the surgical microscope is not required either since the pose of the calibration object need not be known. Expressed differently, the calibration object can be positioned freely in space, i.e., with an unknown pose, for example can be placed on a tabletop.

The creation of the camera model when freely positioning the calibration object in space can be achieved by virtue of the initial pose (calibration object to camera), which is initially unknown on account of the free positioning, being estimated or calculated. Expressed differently, when positioning the calibration object freely in space, the method step of positioning the calibration object in an initial pose in an observation region of the camera of the surgical microscope includes an estimation, e.g., with an initial camera model or nominal camera model, or calculation of the initial pose.

Subsequently, the pose delta for reaching the first pose can be determined and, as already explained, the calibration object can be positioned in the first pose in accordance with the determined pose delta, for example with an appropriate displacement of the camera by way of the robotic stand system.

By contrast, a fixed trajectory is always traversed in calibration methods known from the prior art. This requires the geometric transformation of the pose of the calibration object in relation to a reference point, e.g., the foot of the stand, and hence the initial pose to already been known at the outset, i.e., free positioning the calibration object in space is precisely not possible.

The same calibration object can also be used to create the camera models for a plurality of surgical microscopes or other optical observation devices. By way of example, it is therefore sufficient for a technician to carry along a single calibration object which can be used to create the camera models of different surgical microscopes or optical observation devices, for example at different locations. As a result, the costs of further calibration objects can be saved and use restrictions, as a result of calibration objects being arranged on the optical device, can be avoided.

By way of example, creation of the camera model can be carried out first when putting the surgical microscope into operation and can be subsequently carried out at certain time intervals or depending on certain events, for example transportation, temperature variations, in order to always be able to obtain accurate and reliable measurement results or pose estimates with the camera.

The created camera model can be stored in a memory unit. By way of example, the camera model can be stored on a computer-readable medium.

Optionally, the method can provide for one or more verification steps, in which a check is carried out as to whether the first or a further pose was in fact reached. In the case of a deviation there can be a corresponding correction or repetition. The method overall can also be carried out multiple times in order to achieve a greater accuracy. In this case, the camera model respectively created previously can be used as initial camera model.

According to various embodiment variants, a first number of poses can be located in the region near to the camera and a second number of poses can be located in the region remote from the camera. Typically, the number of poses in the near region may correspond to the number of poses in the remote region in this case.

To obtain the best possible calibration results, recordings should be recorded with the most homogeneous distribution possible over the entire measurement space, ideally having an image in each measurement point. However, this would cause much outlay in terms of time and computation. In order to reduce the outlay but nevertheless map the measurement space representatively, it is possible to record recordings, e.g., only in one plane, typically at a mid-distance. A disadvantage in this case would lie in an under-representation of the distortion, which predominantly occurs in the near region (a small distance between camera and calibration object causes distortions, especially in the edge region). To reduce this effect, recordings can be recorded in two or more planes, for example in the near region and remote region.

By using poses in the near region and remote region, a high accuracy of the camera model is also achieved in these regions. The number of poses in the near region and remote region being the same ensures that no region is over-weighted. Provided the required accuracy of the camera model or calibration quality has already been achieved, it is possible to dispense with poses between the near region and remote region. This can reduce the overall number of poses, and so the camera model can be created quicker and with less computational outlay.

According to further embodiment variants, the poses can be chosen in such a way that the calibration object is positioned fully within the measurement space in each pose. Expressed differently, all characteristic markings to be evaluated can typically be situated within the measurement space.

As a result, the calibration object will advantageously only be imaged on the image sensor of the camera in the required measurement space. Characteristic markings of the calibration object located outside of the measurement space consequently remain unconsidered when creating the camera model, preventing a falsification of the camera model and being able to contribute to higher accuracy of the camera model.

Should characteristic markings of the calibration object nevertheless be located outside of the measurement space and be recorded by the image sensor of the camera, these characteristic markings can be eliminated within the scope of a post-calculation and can remain unconsidered when creating the camera model and during subsequent calibrations.

According to further embodiment variants, the calibration object can be positioned in the measurement space by changing the position of the camera.

Expressed differently, there is the option of not moving the calibration object itself for the purposes of changing the pose vis-à-vis the camera or the measurement space, but of appropriately displacing the measurement space by moving the camera.

As a result, the provided method can be simplified since it is sufficient to position the calibration object once, for example place it on a tabletop. Then, the poses can be adopted by varying the camera position with the stand. This also corresponds to the usual way of handling the surgical microscope since, for example during an operation, it is not the position of the site that is changed but the camera position. Moreover, the use of a robotic stand renders an automation of the method possible, which is connected to the advantages already described above.

A further aspect of the disclosure relates to a method for estimating a pose of an object in a measurement space of a camera of a surgical microscope. In this case, the pose of the object, for example of a surgical instrument, is estimated, for example within the scope of what is known as tool tracking, using a camera model for the camera of the surgical microscope which was created with a method according to the description above. Consequently, the method for estimating the pose is accordingly linked with the advantages of the camera model and the method for creating a camera model, and so reference can be made to the explanations in this context.

The use of such a camera model advantageously facilitates a pose estimate with a high accuracy. In addition, the pose estimate can be wholly or partly carried out in computer-implemented fashion and, as a consequence, in wholly or partly automated fashion. To this end, the camera model can be retrieved from a memory unit in which it is stored. Such a memory unit may be integrated in the surgical microscope or may be signal-connected to the surgical microscope.

Alternatively or in addition, the camera model created with one of the above-described methods can be used for data overlay. To this end, preoperative data can be overlaid in a camera recording using the created representative camera model. The use of a camera model created with one of the above-described methods advantageously facilitates high-accuracy data overlay.

A further aspect of the disclosure relates to a method for verifying a camera model which was created with a method according to the preceding description.

The verification method includes: determining a current pose of a calibration object positioned in a measurement space of a camera of the surgical microscope, defining a target pose for the calibration object, determining a pose delta for reaching the target pose starting from the current pose, changing the current pose of the calibration object in accordance with the determined pose delta, determining a deviation between the set target pose and the actual target pose, and comparing the determined deviation with a limit for a maximum admissible deviation.

The change in the position of the calibration object in accordance with the determined pose delta can be implemented manually, for example by virtue of the determined pose delta being displayed on a monitor and the camera being displaced with the stand following a manual input by the user, for example a servicing technician, hospital staff member, assembly staff member in the manufacturing line. Alternatively, the change in position can be implemented in automated fashion by virtue of the pose delta being implemented by the robotic stand system.

Depending on the application, the limit may be defined on an individual basis and may have an absolute or relative value.

Optionally, the method steps can be repeated in order to be able to determine the deviation for different target poses, for example in the near region and remote region. This may facilitate a more accurate verification of the camera model.

The verification method facilitates a simple and quick verification of the camera model. By way of example, it can be carried out at certain time intervals or on the basis of certain events, for example transport, temperature variation. Should the determined deviation be above the limit, a new camera model can be created forthwith, and so outage times can be reduced, and reliable and reproducible measurement results can moreover be obtained at all times.

In this case, there is the option of reducing the overall number of poses when creating a new camera model, and so the time required for creating the camera model can be reduced.

A further aspect of the disclosure relates to an arrangement comprising a surgical microscope with a camera and means suitable for carrying out one of the methods explained above, i.e., a method for creating a camera model, a method for calibrating the surgical microscope, and/or a method for verifying a calibration.

Consequently, the advantages of the methods are correspondingly connected with the arrangement. Reference is made to the explanations given above.

By way of example, the camera can be a surround camera or a microscope camera. In an exemplary embodiment, the surgical microscope may include both a microscope camera and a surround camera.

Optionally, the surgical microscope may have a stand, likewise as described above, so that automation is rendered possible. The means for carrying out the methods may include a control unit configured and designed to output control signals to the stand and/or the camera for the purposes of carrying out one of the aforementioned methods, for example for positioning the calibration object and/or changing the current pose of the calibration object in accordance with a determined pose delta, a memory unit for storing the camera model and optionally storing the recordings, and a processing unit for processing the recordings made, that is to say for creating the camera model on the basis of the recordings. Optionally, the processing unit can be configured to estimate a pose of an object in the measurement space with the camera model. Further optionally, the processing unit can be designed to define a target pose for the calibration object, determine a pose delta for reaching the target pose starting from the current pose, determine a deviation between the set target pose and the actual target pose, and compare the determined deviation with a limit for a maximum admissible deviation such that a verification of the camera model is rendered possible.

If provision is made for the camera model to be created starting from freely positioning the calibration object in space, the arrangement may include means for estimating or calculating the initial pose. By way of example, the arrangement may include a processing unit which is configured and designed to estimate the initial pose. To this end, the processing unit can use an initial camera model or nominal camera model which is stored in the memory unit and retrieved therefrom, wherefore the processing unit and the memory unit can be operatively signal-connected to one another.

A further aspect of the disclosure relates to a computer program including commands which cause an arrangement according to the description above to carry out one of the methods as explained above, that is to say a method for creating a camera model, a method for estimating a pose of an object in a measurement space of a camera of a surgical microscope, and/or a method for verifying a camera model.

A computer program can be understood to mean a program code that is storable on a suitable medium and/or retrievable from a suitable medium. Consequently, the computer program can be stored on a computer-readable medium, e.g., a computer-readable data medium. Furthermore, a data carrier signal can be formed, which transmits the computer program.

Any medium suitable for storing software, for example a non-volatile non-transitory memory installed in a controller, a DVD, a USB stick, a flash card or the like, can be used to store the program code. By way of example, the program code can be called via the Internet or an intranet or via another suitable wireless or wired network.

BRIEF DESCRIPTION OF THE DRAWINGS

The disclosure will now be described with reference to the drawings wherein.

DESCRIPTION OF EXEMPLARY EMBODIMENTS

Figure 1:
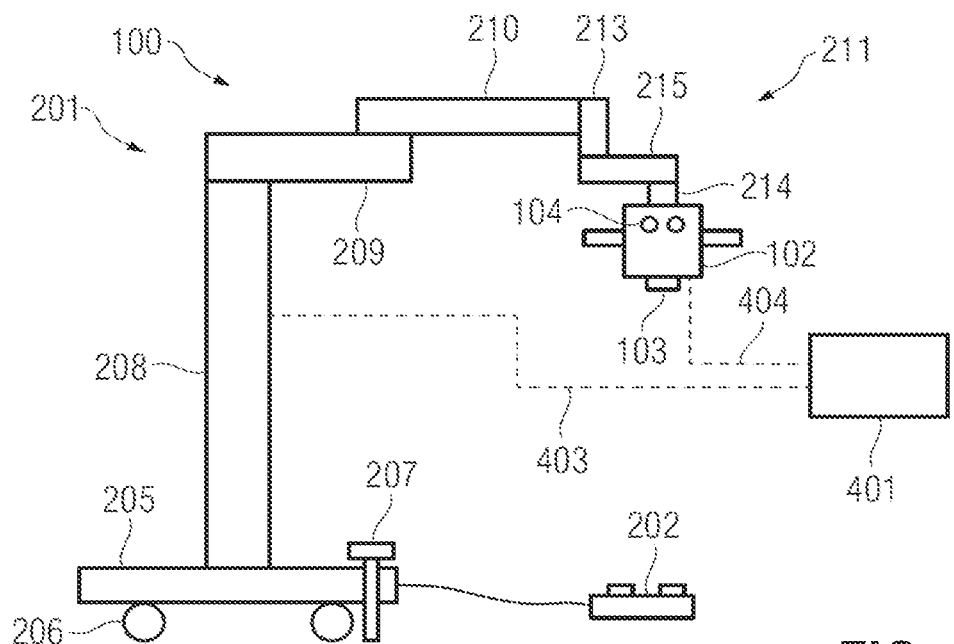
FIG. 1 shows a surgical microscope having a stand and a camera according to an exemplary embodiment of the disclosure.

FIG. 1 depicts a surgical microscope 100 including a motor-driven stand 201 and an optical observation unit 102 fastened to the stand 201 and including a camera 103 and an eyepiece 104. The camera 103 is the microscope camera of the surgical microscope 100, i.e., the main observer. Alternatively, the camera 103 can be a surround camera. Optionally, the surgical microscope 100 can include both a camera 103, e.g., a microscope camera, and a further camera 108 (see FIG. 13), e.g., a surround camera. By entering navigation data, the optical observation unit 102 can be automatically set in terms of its orientation and position, which also allows remote positioning and orientation of the optical observation unit 102 in such a way that a certain section of an object field, e.g., the site, is displayed in optimal fashion. For this purpose, a controller or control unit 401 is assigned to the stand 201, said control unit undertaking the positioning and orientation of the optical observation unit 102 on the basis of received position and/or orientation control data by virtue of control signals 403, 404 being output to suitable actuators.

Below, the stand 201 and the degrees of freedom facilitated by the stand for the optical observation unit 102 are described in more detail on the basis of FIGS. 1 and 2. In the example of a stand 201 shown in FIG. 1, the stand 201 rests on a stand base 205 which has rollers 206 on the lower side thereof, said rollers enabling a displacement of the stand 201. In order to prevent an unwanted displacement of the stand 201, the stand base 205 includes a foot brake 207.

As stand links, the actual stand 201 includes a height-adjustable stand column 208, a support arm 209, a spring arm 210, and a mount 211 for the optical observation unit 102, which in turn includes a connection element 213, a swivel arm 215 and a holding arm 214. The degrees of freedom provided by the stand links for positioning the optical observation unit 102 are shown in FIG. 2. At its one end, the support arm 209 is connected to the stand column 208 in a manner rotatable about an axis A. At the other end of the support arm 209, one end of the spring arm 210 is fastened in a manner rotatable about an axis B that is parallel to the axis A such that the support arm 209 and the spring arm 210 form an articulated arm. The other end of the spring arm 210 is formed by a tilt mechanism (not depicted here), on which the mount 211 is fastened and which enables a tilting of the mount 211 about the axis C.

The mount 211 has an axis of rotation D, a swivel axis E, and a tilt axis F, about which the optical observation unit 102 can be rotated, swiveled, and tilted, respectively. Using a connection element 213, the mount 211 is fastened at the outer end of the spring arm 210 in a manner rotatable about the axis of rotation D. The axis of rotation D extends along the connection element 213. The connection element 213 is adjoined by a swivel arm 215, with the aid of which the optical observation unit 102, more precisely a holding arm 214 which is attached to the swivel arm 215 and on which holding arm the optical observation unit 102 is fastened with a holder (not illustrated), can be swiveled about the swivel axis E. The swivel axis E extends through the swivel arm 215. The angle between the swivel arm 215 and the connection element 213, i.e., the angle between the swivel axis E and the axis of rotation D, can be varied with an adjustment mechanism arranged between the connection part 213 and the swivel arm 215.

The tilt axis F, which enables tilting of the optical observation unit 102, extends through the holding arm 214 in a manner perpendicular to the plane of the illustration. The optical observation unit 102 is fastened to the holding arm 214 with a holder (not illustrated here).

The degrees of freedom of the mount 211 and the adjustment options of the optical observation unit 102, e.g., focusing, sharpness, magnification factor, etc., can be set with an actuating device 202, which is illustrated as a foot control panel in the present exemplary embodiment. However, the actuating device 202 can also be realized as a hand-operated switching element or as a combination of foot- and hand-operated switching element. Moreover, a remote control can be facilitated.

Even if the stand 201 has been described on the basis of a specific example, a person skilled in the art will recognize that differently formed stands can also find use.

Figure 2:
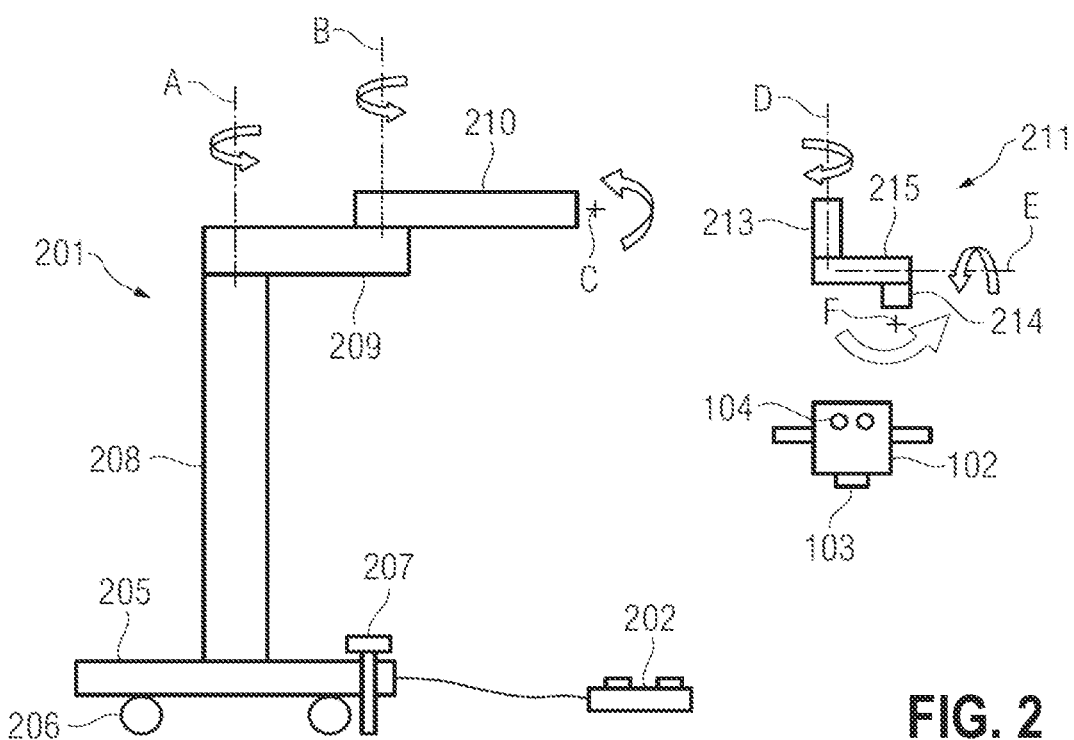
FIG. 2 shows the degrees of freedom provided by the stand of FIG. 1 and its mount.

The camera 103 of the surgical microscope 100 described in exemplary fashion with reference to FIGS. 1 and 2 must be intrinsically calibrated for various measuring methods, i.e., a camera model needs to be created. Optionally, the camera model to be created can be used for further calibrations, e.g., a hand/eye calibration of the camera 103 or a calibration of the kinematic mechanism of the stand 201.

Figure 3:
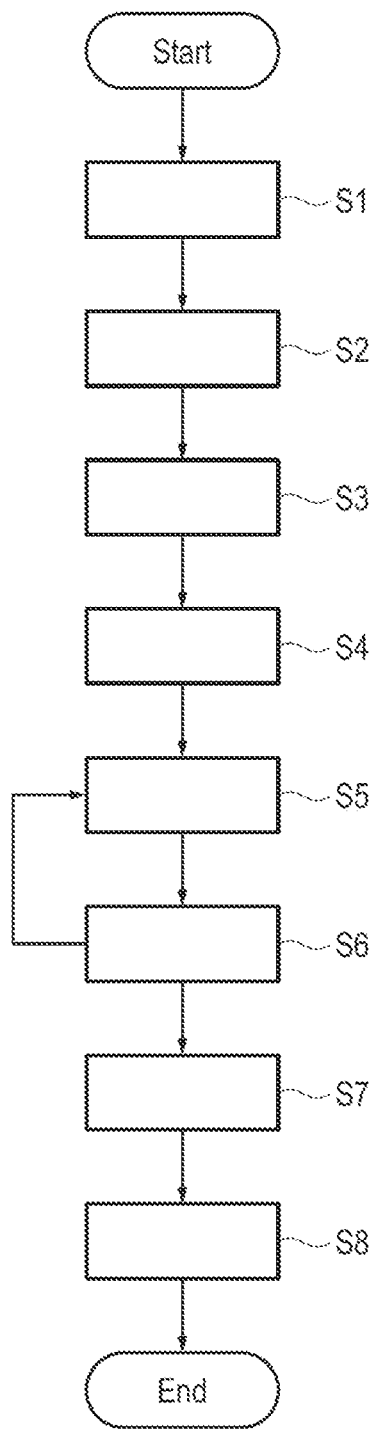
FIG. 3 shows a flowchart of a method for creating a camera model and estimating a pose according to an exemplary embodiment of the disclosure.

An exemplary method for creating a camera model and a method for estimating a pose of an object are explained below with reference to FIGS. 3 to 8. FIG. 3 shows a flowchart in this respect, with the camera model being created in method steps S1 to S7 and the created camera model being used in method step S8 for the purposes of estimating the pose.

A two-dimensional calibration pattern in the form of a chequerboard pattern serves as a calibration object 300 in the exemplary embodiment. Characteristic markings that are usable for creating the camera model are for example those points of the chequerboard pattern where black and white fields are adjacent to one another. Moreover, the dimensions and angles of the black or white fields can also be used for creating the camera model.

Figure 4:
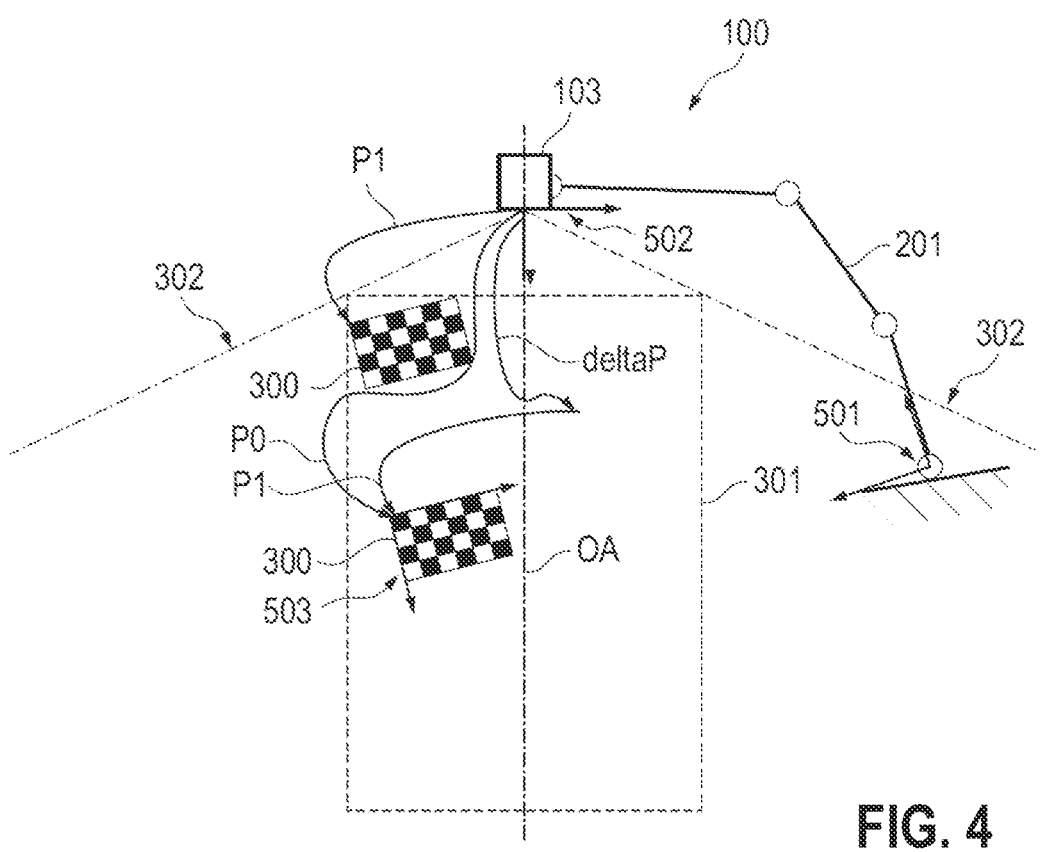
FIG. 4 shows a schematic representation of a surgical microscope and a calibration object in an initial pose.
Figure 5:
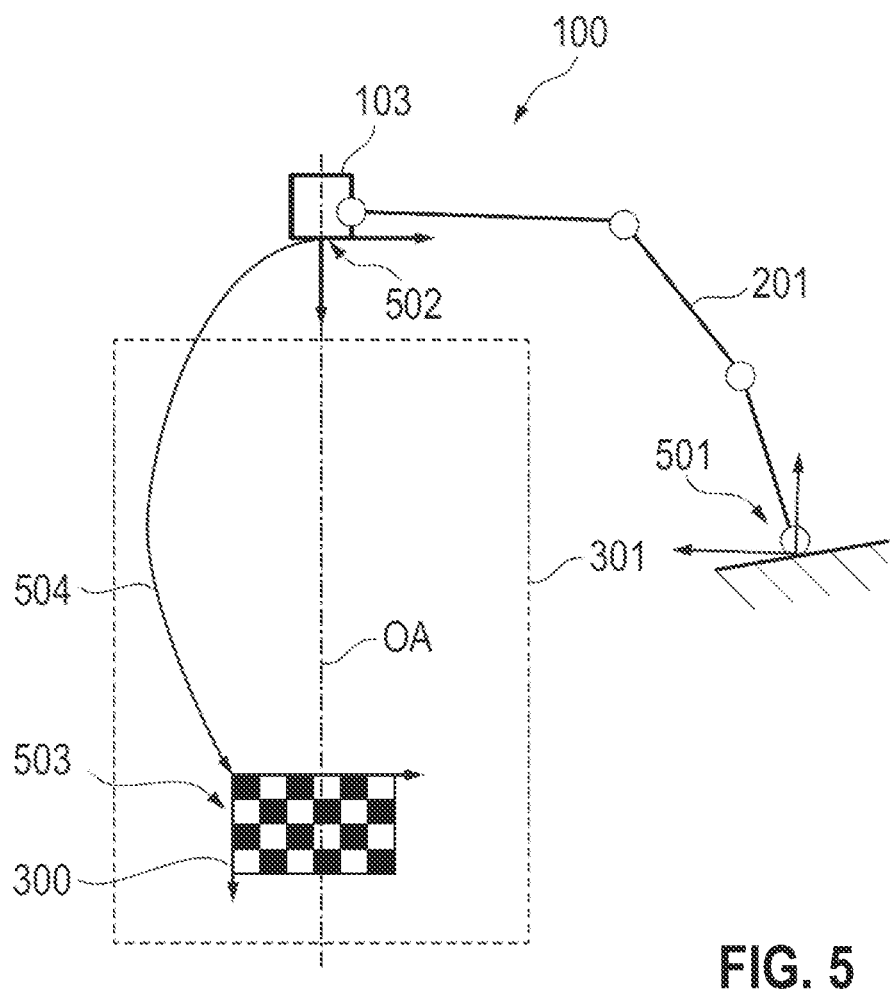
FIG. 5 shows a schematic representation of a surgical microscope and a calibration object while creating a camera model.

In the exemplary embodiment, the measurement space 301 of the camera 103 has a circular cylindrical form, the longitudinal axis of the cylinder corresponding to the optical axis of the camera 103. Consequently, the measurement space 301 is rotationally symmetric in relation to the optical axis OA. The measurement space 301 has a near region 105 and a remote region 106 (see FIG. 6). A mid region 107 is located between the near region 105 and the remote region 106. The measurement space 301 is located within the observation region 302 of the camera 103. In FIG. 4, the limits of the observation region 302 are indicated by a dash-dotted line. The observation region 302 has not been plotted in the remaining figures in order to simplify the representation.

Overall, it is possible to define three different coordinate systems, the base coordinate system 501, the camera coordinate system 502 and the coordinate system of the calibration object 503. The relative position and alignment of the measurement space 301 always remain unchanged within the camera coordinate system 502. To create the camera model, the camera to calibration object 504 vector, that is to say the vector between the coordinate origin of the camera coordinate system 502 and the coordinate origin of the coordinate system of the calibration object 503, is estimated with a pose estimate and an initial camera model to be defined in any desired way, for example a nominal pinhole camera model, which specifies the pose of the calibration object 300 in relation to the camera 103 for an initial pose P0. The camera to calibration object 504 vector defines the initial pose P0 and the poses P1, P2, P3, ..., PN of the calibration object 300.

After the start of the method, the calibration object 300 is positioned with an initial pose P0 in an observation region 302 of the camera 103 of the surgical microscope 100 in method step S1 (see FIG. 4). The initial pose P0 is defined by the associated vector between the coordinate origin of the camera coordinate system 502 and the coordinate origin of the coordinate system of the calibration object 503. In the exemplary embodiment, the calibration object 300 arranged in the initial pose P0 is located within the measurement space 301. However, a positioning outside of the measurement space 301 would also be possible for as long as the calibration object 300 is located in the observation region 302 of the camera 103.

Optionally, the calibration object 300 can be positioned freely in space, for example placed on a table. In this case, the initial pose P0 is estimated with an initial camera model.

In method step S2, the pose delta deltaP that is required to reach the first pose P1 in the measurement space 301 starting from the initial pose P0 is subsequently determined. In method step S3, the calibration object 300 is positioned in the first pose P1. To this end, the camera 103 is moved in accordance with the pose delta deltaP such that the pose of the calibration object 300 changes accordingly.

Subsequently, a recording of the calibration object 300 in the first pose P1 is made with the camera 103 in method step S4. On the basis of the recording, the characteristic markings of the calibration object 300 can be identified and evaluated subsequently within the scope of creating the camera model.

Subsequently, the calibration object 300 is positioned in the measurement space 301 in a further pose P2 (method step S5) and another recording of the calibration object 300 is made with the camera 103 (method step S6). Method steps S5 and S6 are repeated until the calibration object 300 has been positioned in the desired number of poses P1, P2, P3, ..., PN and the corresponding recordings were made.

In subsequent method step S7, the camera model is created on the basis of the recordings made. To this end, important parameter values, for example the distance between the image sensor of the camera 103 and the optical center and the distortion coefficients, are determined. In method step S7, the camera model or the parameters contained therein are used to estimate a pose of an object in the measurement space 301 of the camera 103.

Figure 6:
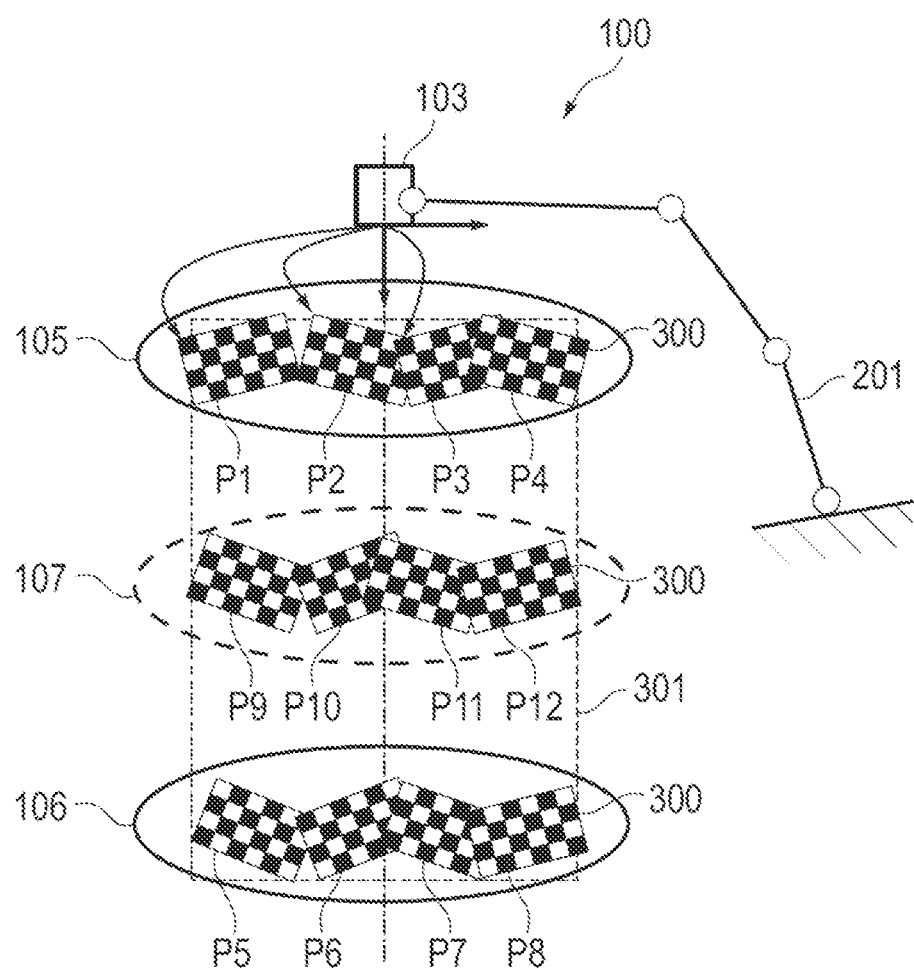
FIG. 6 shows a schematic representation of the surgical microscope during the creation of the camera model, with various poses of the calibration object.
Figure 7A:
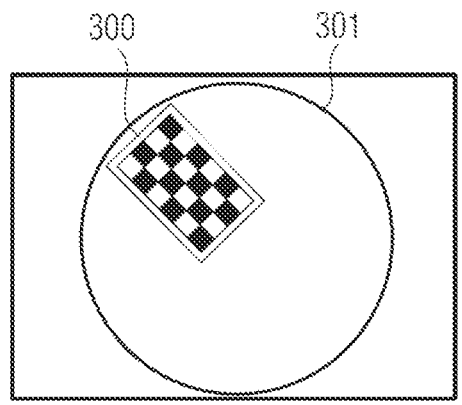
FIGS. 7A to 7D show various poses of the calibration object in the near region.
Figure 7B:
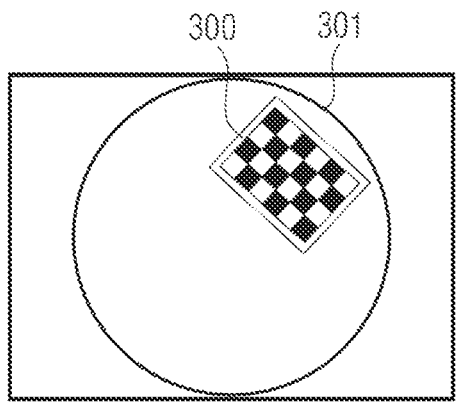
Figure 7C:
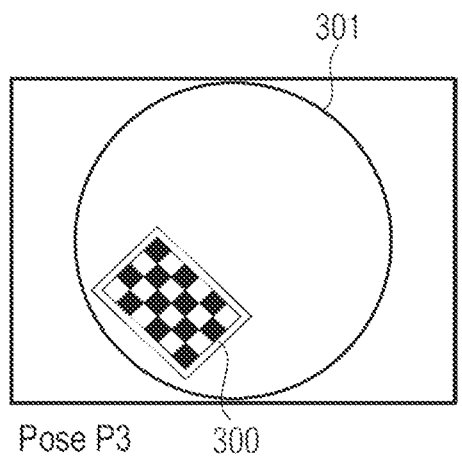
Figure 7D:
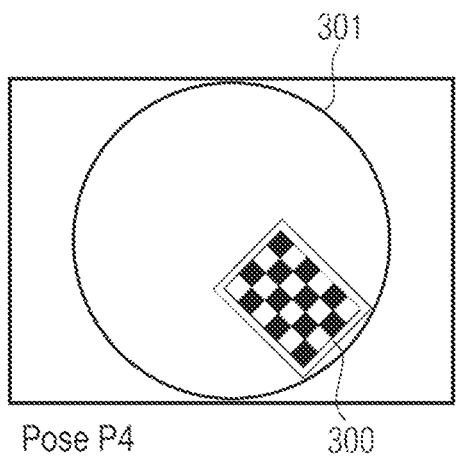
Figure 8A:
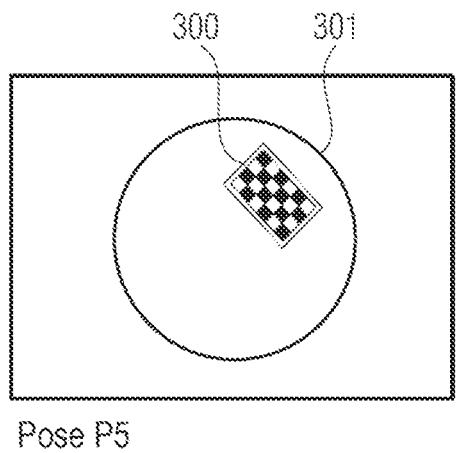
FIGS. 8A to 8D show various poses of the calibration object in the remote region.
Figure 8B:
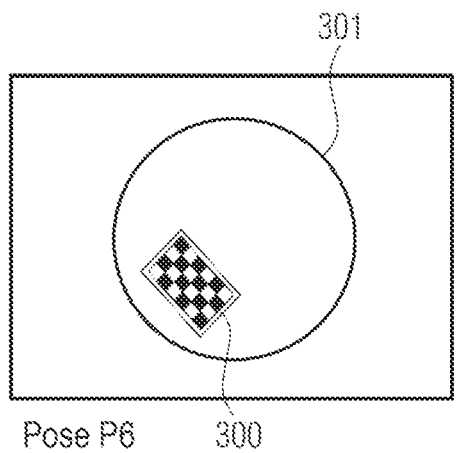
Figure 8C:
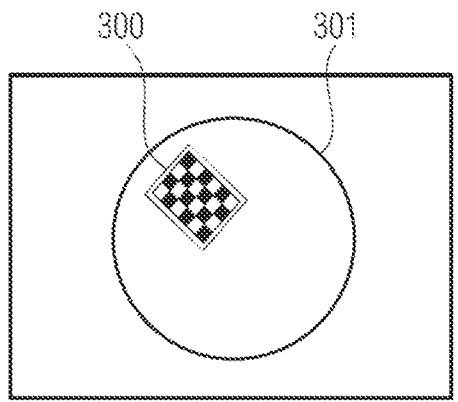
Figure 8D:
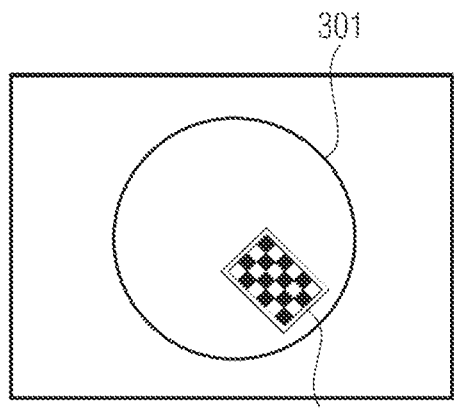

With reference to FIGS. 6 to 8, the selection of the poses P1, P2, P3, ..., PN is explained in more detail below. According to an aspect of the disclosure, provision is made for the first pose P1 and the further poses P2, P3, ..., PN to be chosen with such a distribution in the measurement space 301 that a camera model is obtained which is representative in relation to the entire measurement space 301. The specific sequence in which the poses P1, P2, P3, ..., PN are adopted is irrelevant to the camera model to be created since the recordings of all poses P1, P2, P3, ..., PN are taken into account with equal weighting in the camera model. However, a typical sequence of poses P1, P2, P3, ..., PN may arise for reasons of saving time, that is to say it may be advantageous to use the pose with the smallest distance from the current pose P1, P2, P3, ..., PN as next pose P1, P2, P3, ..., PN. In principle, any pose P1, P2, P3, ..., PN can be used as first pose P1.

In the exemplary embodiment, this is achieved by virtue of the calibration object 300 being positioned in a total of eight poses P1, P2, P3, P4, P5, P6, P7, P8 and corresponding recordings being made. Of these poses, four poses P1, P2, P3, P4 are in the near region 105 (see FIGS. 7A to 7D) and four poses P5, P6, P7, P8 are in the remote region 106 (see FIGS. 8A to 8D). The four poses P1, P2, P3, P4 in the near region 105 are arranged in a plane and the four poses P5, P6, P7, P8 in the remote region are arranged in a plane. In twos, the poses P1, P2, P3, P4, P5, P6, P7, P8 are moreover arranged rotationally symmetrically in relation to the optical axis OA (poses P1 and P4 and poses P2 and P3 in FIG. 7, and poses P5 and P6 and poses P7 and P8 in FIG. 8). An averaged camera model, in which no region is overweighted, is created by virtue of using the same number of recordings in the near region 105 and in the remote region 106 for the creation of the camera model.

Optionally, additionally poses P9, P10, P11, P12 may be recorded in the mid region 107 (see FIG. 6) in order to be able to obtain a more robust camera model. The overall number of the poses P1, P2, P3, P4, P5, P6, P7, P8 used in the exemplary embodiment should merely be understood to be exemplary. Overall, more or fewer poses P1, P2, P3, ..., PN can be used depending on the required quality of the camera model, for as long as these poses are chosen in such a way that a camera model that is representative in relation to the entire measurement space is obtained.

Moreover, all poses P1, P2, P3, ..., PN are chosen in such a way in the exemplary embodiment that the calibration object 300 is fully positioned within the measurement space 301 in each pose P1, P2, P3, ..., PN. The various poses P1, P2, P3, ..., PN are positioned in the measurement space 301 by changing the position of the camera 103. This means that the pose P1, P2, P3, ..., PN of the calibration object 300 remains unchanged in relation to the base coordinate system 501 while the position of the camera 103 is changed in order to change the position of the measurement space 301 and consequently also the pose P1, P2, P3, ..., PN of the calibration object 300 in the measurement space 301. As described with reference to FIGS. 1 and 2, the position of the camera 103 is changed with the stand 201. This facilitates automation of the method for creating the camera model.

Figure 9:
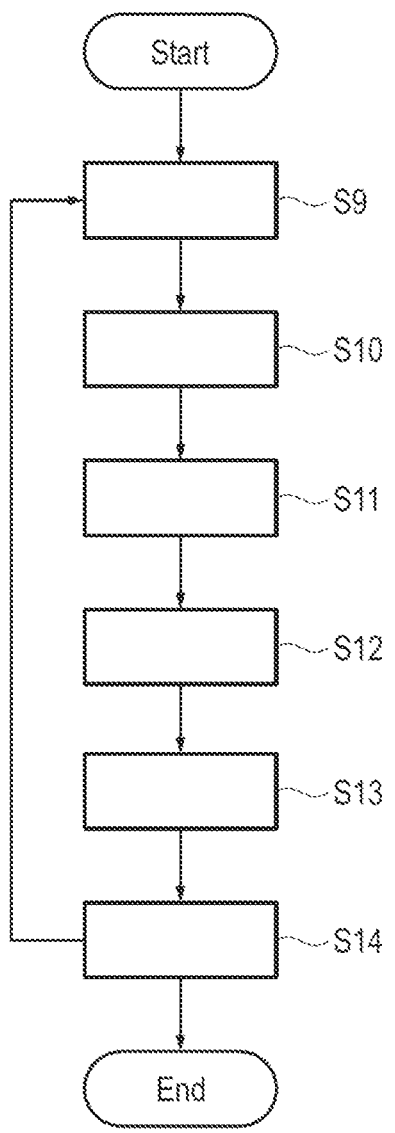
FIG. 9 shows a flowchart of an exemplary method for verifying a camera model.
Figure 10:
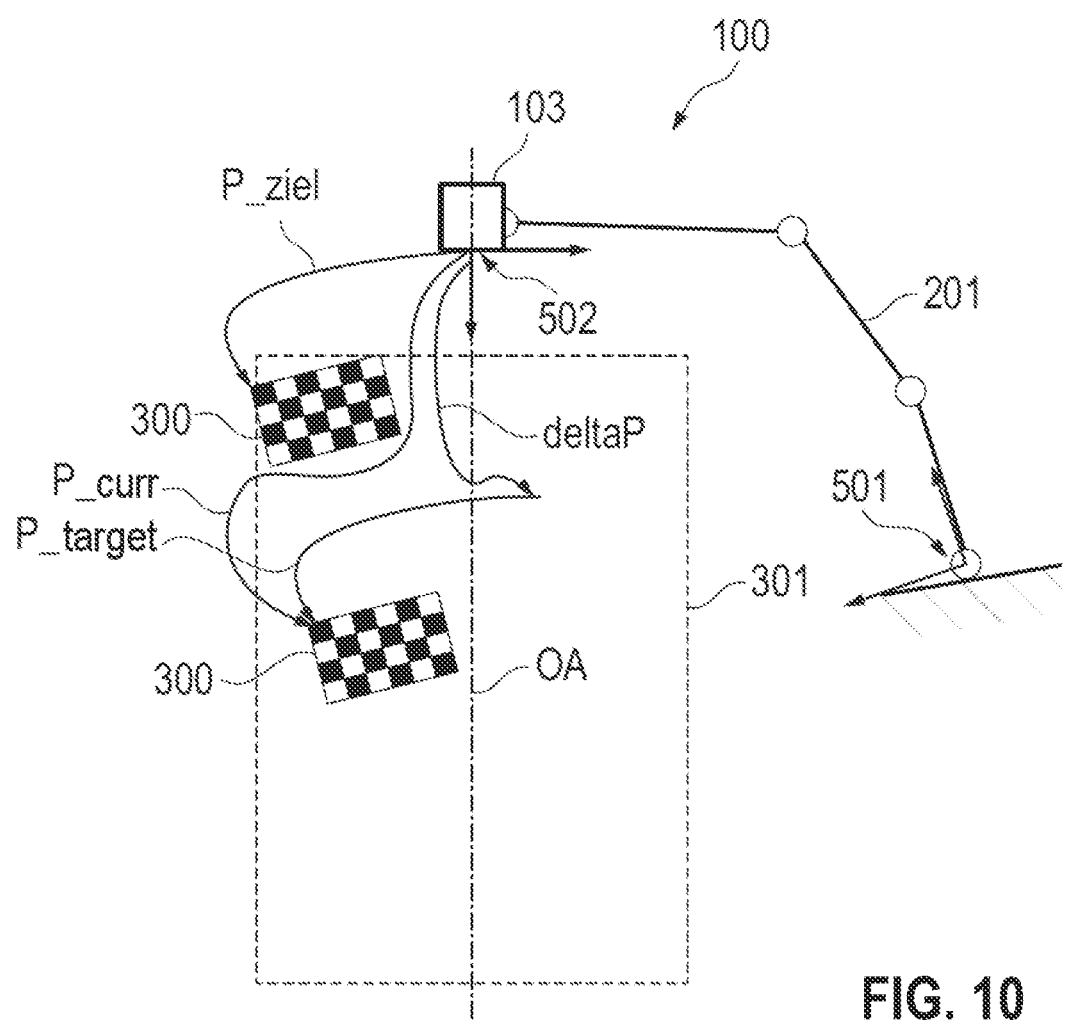
FIG. 10 shows a schematic representation of a surgical microscope and a calibration object in a current pose.
Figure 11:
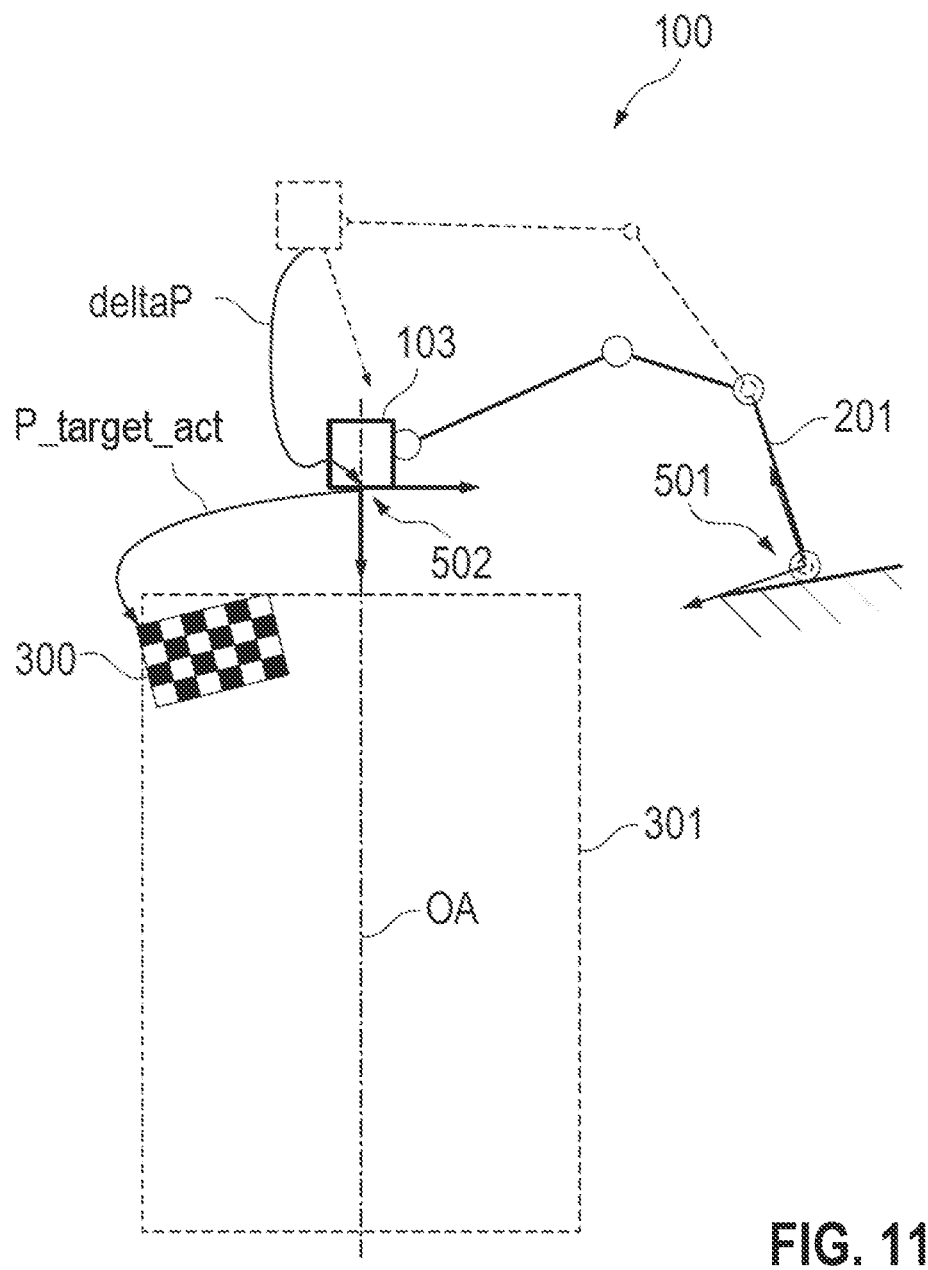
FIG. 11 shows a schematic representation of the surgical microscope and the calibration object in a target pose.

An exemplary method for verifying a camera model is described below with reference to FIGS. 9 to 11. By way of example, this can be the camera model obtained above with reference to FIGS. 3 to 8. For elucidation of the surgical microscope 100, reference is made to the explanations in relation to FIGS. 1 and 2.

In a first method step S9, the current pose P_curr of the calibration object 300 positioned in the measurement space 301 of the camera 103 of the surgical microscope 100 is determined. Expressed differently, the current relative pose of the calibration object 300 in relation to the camera 103 is determined on the basis of an available camera model which is intended to be verified (see FIG. 10). A desired target pose P_target for the calibration object 300 in the measurement space 301 is defined in the next method step S10. Method steps S9 and S10 can also be carried out in reverse sequence or simultaneously.

Subsequently, the pose delta deltaP for reaching the target pose P_target starting from the current pose P_curr is determined in method step S11. Expressed differently, the vector according to which the calibration object 300 needs to be moved to convert the current pose P_curr into the target pose P_target is determined.

In method step S12, the current pose P_curr of the calibration object 300 is changed in accordance with the determined pose delta deltaP. Optionally, this can be carried out manually or in automated fashion. In the case of a manual execution, the determined pose delta deltaP can be displayed on a monitor. Subsequently, the camera 103 is manually displaced by a user, for example a service technician, a hospital staff member, an assembly colleague, in such a way that the calibration object 300 is positioned in the measurement space 301 in accordance with the target pose P_target. In the case of an automated embodiment, the pose delta deltaP is controlled with the robotic stand 201, which moves the camera 103 accordingly. FIG. 11 shows the calibration object 300 in the actually reached target pose P_target_act and the movement path (dashed arrow) of the camera 103 for reaching the actual target pose P_target_act.

Subsequently, the deviation between the defined target pose P_target and the actual target pose P_target_act is determined in method step S13 and compared to a limit for a maximally admissible deviation (method step S14). Expressed differently, a check is carried out as to whether the actual target pose P_target_act has the desired value, that is to say whether the difference between the target pose P_target and the actual target pose P_target_act is below a set limit or within a specified tolerance range. The determined deviation can be considered a measure for the quality of the camera model.

Method steps S9 to S14 can subsequently be repeated for a specifiable number of target poses P_target in order to be able to obtain more reliable statements about the current calibration. To this end, target poses P_target can be chosen in the near region 105 and in the remote region 106, and optionally additionally in the mid region 107. The sequence of the target poses P_target can be chosen freely. The sequence of the target poses P_target can typically be chosen in such a way that the duration of a calibration journey, i.e., the time taken to home in on all desired target poses P_target, is as short as possible.

If the limit is exceeded, that is to say the demanded quality is not achieved, the camera model can be created anew, for example using the method explained above with reference to FIGS. 3 to 8.

Figure 12:
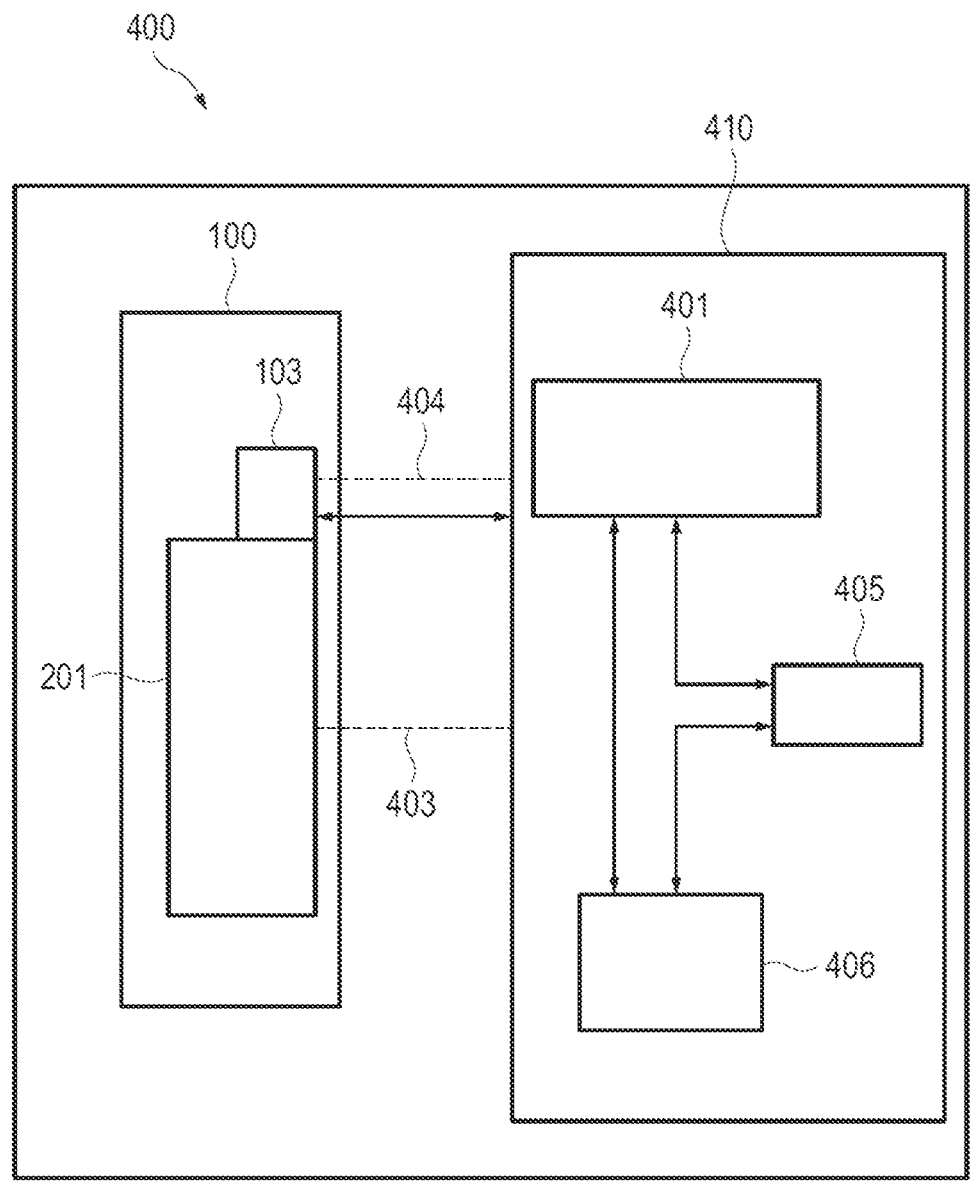
FIG. 12 shows a schematic representation of an arrangement according to an exemplary embodiment of the disclosure.

FIG. 12 shows an exemplary arrangement 400 in a schematic representation. This arrangement 400 can be used to carry out the methods described above with reference to FIGS. 3 to 11 and can be designed accordingly.

The arrangement 400 includes a surgical microscope 100 with a camera 103 and a stand 201. For more details, reference is made in exemplary fashion to FIGS. 1 and 2 and the associated description. Moreover, the arrangement includes means 410 which are suitable for carrying out the steps of a method for creating a camera model for a camera of a surgical microscope 100, of a method for estimating a pose of an object in a measurement space 301 of the camera 103 of the surgical microscope 100 and of a method for verifying the camera model. These means 410 include a control unit 401, a processing unit 405, and a memory unit 406, which are operatively signal connected to one another, indicated in FIG. 11 by double-headed arrows.

As already explained with reference to FIGS. 1 and 2, the control unit 401 can output control signals 403, 404 to the camera 103 and the stand 201. This firstly facilitates the triggering of the camera 103 required to make the recordings of the calibration object 300 and secondly facilitates the positioning of the camera 103 by an appropriate movement of the stand 201. Furthermore, there is an operative signal-connection between the camera 103 and the means 410, for example in order to be able to store recordings of the camera 103 in the memory unit 406 and process these in the processing unit 405.

The signal transmission can be implemented in wired or wireless fashion in each case, for example using radio signals. Corresponding transmission and reception devices are not shown in FIG. 12, but they may have a design that is conventional in the art. As a consequence, the means 410 need not necessarily be arranged spatially adjacent to the surgical microscope, but may also be present remotely, e.g., in centralized fashion. This also facilitates a common use of the means 410 by a plurality of surgical microscopes 100. Additionally, the means 410 need not necessarily be arranged in spatially adjacent fashion. By way of example, there is the option of the control unit 401 being arranged spatially adjacent to the surgical microscope 100 (see FIG. 1) while the memory unit 406 and the processing unit 405 may be arranged spatially remotely.

Figure 13:
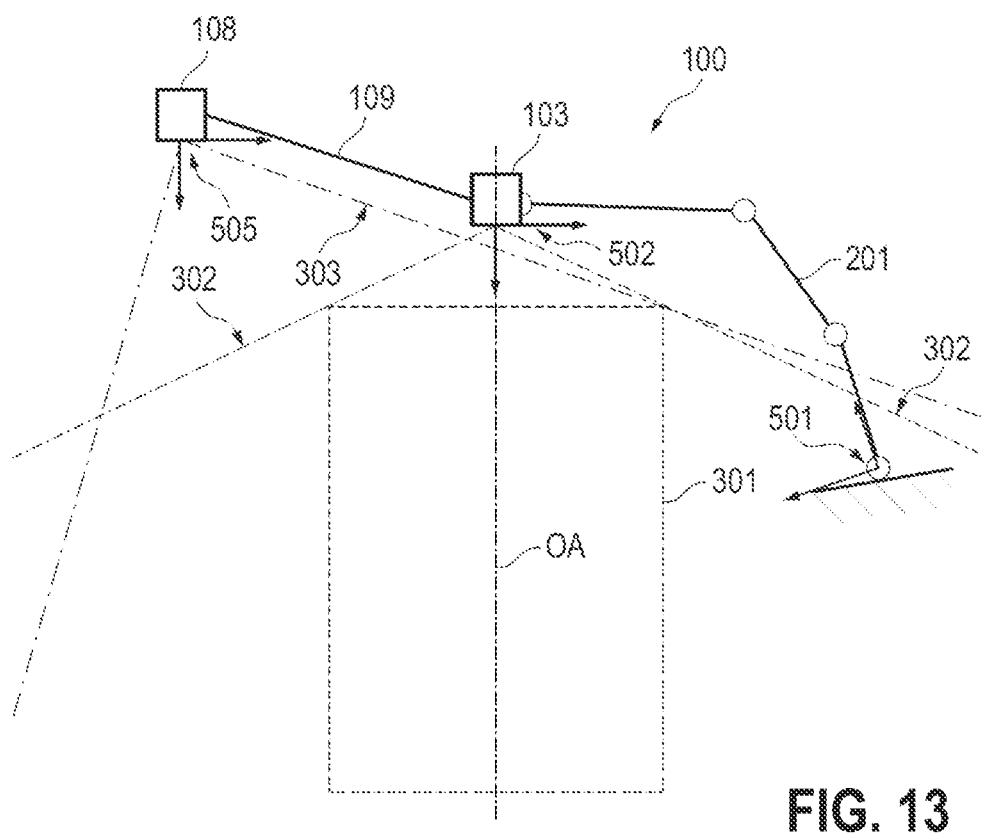
FIG. 13 shows a schematic representation in relation to an alternative definition of the measurement space.

FIG. 13 shows a surgical microscope 100 which has a further camera 108 in addition to the camera 103, which is a microscope camera. The further camera 108 is a surround camera with an associated coordinate system 505. In FIG. 13, the observation region 303 of the further camera 108 is depicted by a dash-dotted line. The camera 103 and the further camera 108 are securely connected to one another by way of a connection 109 such that the pose of the two cameras 103, 108 with respect to one another is unchangeable and a rigid transformation between the two cameras 103, 108 is facilitated.

As described above, a camera model can be created for the camera 103. Optionally, a camera model can additionally be created for the further camera 108 by virtue of implementing a suitable geometric transformation from the coordinate system 502 of the camera 103 to the coordinate system 505 of the further camera 108.

Overall, the present disclosure offers, inter alia, the following advantages:

The process for creating the camera model is fully automatable. As a result, a higher reproducibility can be obtained vis-à-vis random recordings.

Recordings of the calibration object in the measurement space chosen in targeted fashion facilitate the creation of a camera model that is representative for the entire measurement space.

The accuracy of the camera model can be increased since poses of the calibration object (vector from camera to calibration object) can be homed in on in targeted fashion.

The provided method for creating the camera model only requires one calibration object with a known geometry. The calibration object may also be depicted on a monitor.

Should the camera model be changed as a result of the influence of temperature or transport, there can be an automated verification of the camera model in the field, for example by the hospital staff or within the scope of remote maintenance. The number of poses could be reduced to this end. This reduces the amount of time required.

In the case of automation, there is no need for manual movement of the calibration object or surgical microscope.

The present disclosure has been explained in detail on the basis of exemplary embodiments for explanatory purposes.

However, a person skilled in the art will appreciate that they may depart from details of these exemplary embodiments.

Since it is possible to deviate from the individual described exemplary embodiments in a manner evident to a person skilled in the art, the present disclosure should not be restricted by the described exemplary embodiments, but merely by the attached claims.

The expression "and/or" used here, when it is used in a series of two or more elements, means that any of the elements listed can be used alone, or any combination of two or more of the elements listed can be used.

LIST OF REFERENCE NUMERALS

100 Surgical microscope
102 Optical observation unit
103 Camera
104 Eyepiece
105 Near region
106 Remote region
107 Mid region
108 Further camera
109 Connection
201 Stand
202 Actuating device
205 Stand base
206 Rollers
207 Foot brake
208 Stand column
209 Support arm
210 Spring arm
211 Mount for the optical observation unit
213 Connection element
214 Holding arm
215 Swivel arm
300 Calibration object
301 Measurement space
302 Observation region of the camera
303 Observation region of the further camera
400 Arrangement
401 Control unit
403 Control signal
404 Control signal
405 Processing unit
406 Memory unit
410 Means
501 Base coordinate system
502 Camera coordinate system
503 Coordinate system of the calibration object
504 Vector from camera to calibration object
505 Coordinate system of the further camera
A Axis of rotation
B Axis of rotation
C Tilt axis
D Axis of rotation
E Swivel axis
F Tilt axis
OA Optical axis
P0 Initial pose
P1, P2, . . . , PN Pose
P_curr Current pose
P_target Defined target pose
P_target_act Actual target pose
deltaP Pose delta
S1 to S14 Method steps

What is claimed is:

1. A method for creating a camera model for a camera of a surgical microscope, the method comprising:
    positioning a calibration object in an initial pose in an observation region of the camera of the surgical microscope;
    determining a pose delta for reaching a first pose for the calibration object in a measurement space of the camera starting from the initial pose, the measurement space being defined as a volume to be observed with the camera, wherein the pose delta corresponds to a first vector defining a movement of the calibration object from the initial pose to the first pose;
    positioning the calibration object in the first pose in accordance with the pose delta by changing a pose of the camera in accordance with the first vector;
    making a first recording of the calibration object in the first pose with the camera;
    positioning the calibration object in at least one further pose in the measurement space of the camera in accordance with a second vector defining the movement of the calibration object from the first pose to the at least one further pose by changing the pose of the camera in accordance with the second vector;
    making a second recording of the calibration object in the at least one further pose with the camera;
    creating the camera model based on the first and second recordings; and
    the first pose and the at least one further pose being chosen with a distribution in the measurement space such that a camera model is obtained which is representative in relation to the entire measurement space.

2. The method according to claim 1, wherein a first number of poses are located in a first region near to the camera and a second number of poses are located in a second region remote from the camera.

3. The method according to claim 2, wherein the first number of poses in the first region near to the camera corresponds to the second number of poses in the second region remote from the camera.

4. The method according to claim 1, wherein the initial, first, and at least one further poses are selected such that the calibration object is positioned fully within the measurement space in each of the initial, first, and at least one further poses.

5. The method according to claim 1, wherein characteristic markings of the calibration object located outside of the measurement space remain unconsidered when creating the camera model.

6. The method according to claim 1, wherein the calibration object is positioned in the measurement space by changing the position of the camera.

7. The method according to claim 1, wherein the measurement space has a cylindrical or cuboid form.

8. The method according to claim 1, wherein:
    the camera model is a first camera model, and
    the method further comprises creating a further camera of the surgical microscope based on the first camera model.

9. The method according to claim 1, wherein the calibration object is positioned freely in space.

10. A method for estimating the pose of an object in the measurement space of the camera of a surgical microscope, the method comprising:
    estimating the pose with the camera model for the camera of the surgical microscope, the camera model having been created with the method according to claim 1.

11. A method for verifying the camera model, the camera model having been created with the method according to claim 1, the method comprising:
  determining a current pose of the calibration object positioned in the measurement space of the camera of the surgical microscope;
  defining a target pose for the calibration object;
  determining the pose delta for reaching the target pose starting from the current pose;
  changing the current pose of the calibration object in accordance with the pose delta;
  determining a deviation between the target pose and an actual target pose; and
  comparing the deviation with a limit for a maximum admissible deviation.

12. An arrangement, comprising:
  a surgical microscope having a camera, and
  means for carrying out the method according to claim 1.

13. The arrangement according to claim 12, wherein the camera is a surround camera or a microscope camera.

14. A non-transitory computer-readable storage medium encoded with a computer program comprising executable commands that when executed by the arrangement according to claim 12 cause the arrangement to:
  position a calibration object in an initial pose in an observation region of the camera of the surgical microscope;
  determine a pose delta for reaching a first pose for the calibration object in a measurement space of the camera starting from the initial pose, the measurement space being defined as a volume to be observed with the camera;
  position the calibration object in the first pose in accordance with the pose delta;
  make a first recording of the calibration object in the first pose with the camera;
  position the calibration object in at least one further pose in the measurement space of the camera;
  make a second recording of the calibration object in the at least one further pose with the camera;
  create a camera model based on the first and second recordings; and
  the first pose and the at least one further pose being chosen with a distribution in the measurement space such that a camera model is obtained which is representative in relation to the entire measurement space.

* * * * *